(12) United States Patent
Schafer

(10) Patent No.: US 6,473,170 B2
(45) Date of Patent: Oct. 29, 2002

(54) LINEAR OPTICAL SENSOR FOR A CLOSURE

(75) Inventor: Thomas C. Schafer, Des Plaines, IL (US)

(73) Assignee: White Cap, Inc., Downers Grove, IL (US)

(*) Notice: Subject to any disclaimer, the term of this patent is extended or adjusted under 35 U.S.C. 154(b) by 70 days.

(21) Appl. No.: 09/766,201

(22) Filed: Jan. 19, 2001

(65) Prior Publication Data

US 2002/0097396 A1 Jul. 25, 2002

(51) Int. Cl.[7] ................................. G01N 21/90
(52) U.S. Cl. ................................. 356/240.1; 250/223 B
(58) Field of Search ................... 356/239.4, 240.1, 356/428; 250/223 B (56) References Cited

U.S. PATENT DOCUMENTS

| | | |
|---|---|---|
| 2,472,945 A | 6/1949 | Gingrich |
| 2,982,862 A | 5/1961 | Smith |
| 3,133,638 A | 5/1964 | Calhoun |
| 3,365,699 A | 1/1968 | Foster |
| 3,454,759 A | 7/1969 | Calhoun |
| 3,469,689 A | 9/1969 | O'Neil, Jr. |
| 3,756,404 A | 9/1973 | King et al. |
| 3,955,179 A | 5/1976 | Planke |
| 4,391,373 A | 7/1983 | Wiggins |
| 5,171,979 A | 12/1992 | Kwa et al. |
| 5,204,911 A | 4/1993 | Schwartz et al. |
| 5,369,713 A | 11/1994 | Schwartz et al. |
| 5,637,864 A | 6/1997 | Nicks et al. |
| 5,699,162 A | 12/1997 | Pirani et al. |
| 5,730,298 A * | 3/1998 | Gernet et al. ............ 356/240.1 |
| 5,864,600 A | 1/1999 | Gray et al. |
| 5,895,911 A | 4/1999 | Giometti et al. |
| 5,896,195 A * | 4/1999 | Juvinall et al. ............ 356/240.1 |
| 5,987,161 A | 11/1999 | Doane et al. |
| 6,104,482 A | 8/2000 | Brower et al. |

OTHER PUBLICATIONS

Keyence Sensors Vision Systems & Measuring Instruments for Industrial Automation Catalog No. KAG5, pp. 406–411 (1999–2000).

Tap Tone 100 On–Line Inspection System Brochure by Benthos, Inc., dated Oct., 1998.

Tap Tone 100 Package Inspection Brochure by Benthos, Inc., dated Nov., 1999.

Tap Tone 500 Package Inspection Brochure by Benthos, Inc., dated Mar., 2000.

Tap Tone Package Inspection (Tap Tone 500, Proximity Technology and Laser Technology), pages from Internet Web Site www.benthos.com.

* cited by examiner

*Primary Examiner*—Richard A. Rosenberger
(74) *Attorney, Agent, or Firm*—Cook, Alex, McFarron, Manzo, Cummings & Mehler, Ltd.

(57) ABSTRACT

A method and apparatus for detecting the presence of a closure on a container and determining whether the closure is properly seated includes at least two fiber optic heads positioned opposite one another on either side of a conveyor belt or other package transport mechanism. The optic heads face one another through the path of travel of a package. The optic fibers of the receiving head are arranged in a rectangular shape, narrow in the horizontal direction and long in the vertical direction. The optic heads are connected to an optical sensor with an analog output. As a package with a closure travels down the transport mechanism, the package closure interrupts portions of the light beam directed at the receiving head. The optical sensor generates an analog trace signal as the closure moves down the conveyor. A processor samples the analog signal and determines the presence and/or position of the closure therefrom.

18 Claims, 8 Drawing Sheets

FIG. 1

FIG. 2(a)
VIEW A-A

LINEAR OPTICAL SENSOR FOR A CLOSURE

FIELD OF THE INVENTION

The present invention is directed at an inspection system for packages. In particular, the present invention is directed at a method and apparatus for detecting the presence of a closure on a container and determining whether the closure is properly seated on the container.

BACKGROUND OF THE INVENTION

In the packaging industry, the quality and preservation of packaged goods depend a great deal upon the quality of the package. One important aspect of package quality is the effectiveness of the closure at sealing the product in the container and protecting it from outside elements. A cocked closure, for example, may allow air and other elements into the container and in contact with the product, resulting in spoilage and/or a reduction in quality or freshness or other adverse effect. Also, a loose fit closure may easily become detached from the container and lead to product spillage. On the other hand, a closure that is set too tight may become difficult or seemingly impossible to remove by the consumer resulting in consumer frustration with the product. Closure set may affect other aspects of product packaging, such as the application of a safety seal around the closure, or packaging and product stacking, for example.

Today, automation processes are commonplace for filling containers and packages with a product and securing closures on the containers and packages. Modern equipment can fill containers and apply closures at rates from 300 to 2000 containers per minute and beyond. After a product, which may be a solid, liquid, or gas, is dispensed into a container, a closure is applied to the opening of the container and secured thereto using any one of a number of closure application mechanisms known in the art. Also, safety seals and/or tamper-proofbands may be applied to the container and/or closure before or after the closure is secured to the container. As is well known in the art, the dispensing of the product into the container and the application of the closure on the container, as well as any other seals and/or bands, is performed automatically by machines. Occasionally, the closure is not set properly on the container or is missing. Upon such an occurrence, the package is referred to as a "dud".

Several devices/mechanisms exist for testing a completed package (e.g., to verify that the fill level is within tolerance, the labels are properly positioned, the container is intact and the closure is properly seated). Typically, a package that does not conform to specifications is rejected for disposal or correction.

Devices for testing completed product packages, including jars and bottles, include optical sensors, proximity detectors, linear array cameras, radiation detectors, lasers, and other devices. For example, U.S. Pat. No. 5,895,911 discloses a glass container body detector for locating checks in the bodies of glass containers. It includes a light source and linear array cameras. U.S. Pat. No. 5,864,600 discloses a system having a radiation source and a radiation detector wherein a container situated or moving therebetween blocks portions of the radiation. The radiation detector generates electric signals in response to receiving portions of the radiation not blocked by the container. Processing circuitry determines one or more characteristics of the container from the set of characteristics of a standard container. U.S. Pat. No. 5,369,713 discloses a method for detecting defects in stationary products or products moving on a production line. The product is illuminated by a light source and an image of the product is taken by a sensor. The processor examines areas of interest of the product image and data analysis determines whether a cap is in place and aligned. Also, U.S. Pat. No. 4,472,945 discloses an apparatus for detecting uncapped bottles in which light from a light source located above a bottle is reflected off a cap to a photo tube.

Given the importance of having a closure properly seated on a container and the pace at which modern packaging systems operate, there is a continuing need to have rapid and accurate package inspection systems for ascertaining the position and attitude of a closure on a container.

OBJECT OF THE INVENTION

Accordingly, it is an object of the present invention to provide a method and apparatus for determining the position and attitude of a closure on a container.

It is also an object to provide an apparatus that is sturdy in a package inspection system environment, performs accurately and consistently, and can be easily adjusted to accommodate variations that occur in such a system, such as container height and closure size. Still further objects and measures of the invention will become apparent after consideration of an ensuing description and accompanying drawings.

DETAILED DESCRIPTION OF THE PREFERRED EMBODIMENT

The optical closure position sensing system of the present invention provides a data signal representative of the horizontal profile of a closure sealing a container. As explained below, the horizontal profile data signal is used to detect packages having missing, cocked, or high closures. The closure profile provides an indication of the vertical height of the closure as applied to the container, and thus whether the closure is appropriately tightened. For example, a consistent closure profile of 4.0 volts along the length of the closure may indicate that the closure is level (because the signal is steady) and tightened to the proper depth on the container (because of the amount of light received by the optical sensor). In this example, an output level greater than 4.0 volts (e.g., 7.0 volts) may indicate that the closure is missing (i.e., more light received because no light is blocked by the missing closure), while a relatively lower output level (e.g., 1.0 volt) would indicate that the closure is not tightened down. As another example, a profile that increases or decreases along the length of the closure indicates a cocked closure. It will be understood that the linear optical closure position sensing system of the present invention may be used for metal and plastic closures, or any closure that blocks light.

The linear optical closure position sensing system of the present invention, discussed in more detail below, preferably includes a light source and a fiber optic head having a plurality of optical fibers arranged linearly therein. The fiber optic head is positioned proximate to a container having a closure thereon. The optic head and container/closure cooperate to provide a closure trace as light is transmitted toward the container/closure assembly and received by the optic head. The fiber optic head thereby generates signals indicative of the position and attitude of the closure on the container.

Preferably, the light source and sensor are positioned opposite each other a predetermined distance above a moving conveyor or other package transport mechanism. A package on the conveyor blocks at least a portion of the light transmitted from a light source to the linear receiver head. The light that is not blocked is transmitted to an optical sensor. The optical sensor provides an output signal having a magnitude that is proportional (or inversely proportional) to the amount of light received as the closure passes thereby. Because the optic fibers are arranged in a linear configuration that is (substantially) vertically oriented, the amount of light received by the fiber optic head is highly dependent upon the vertical displacement of the portion of the closure that is blocking light directed at the fiber optic head receiver.

Figure 1:
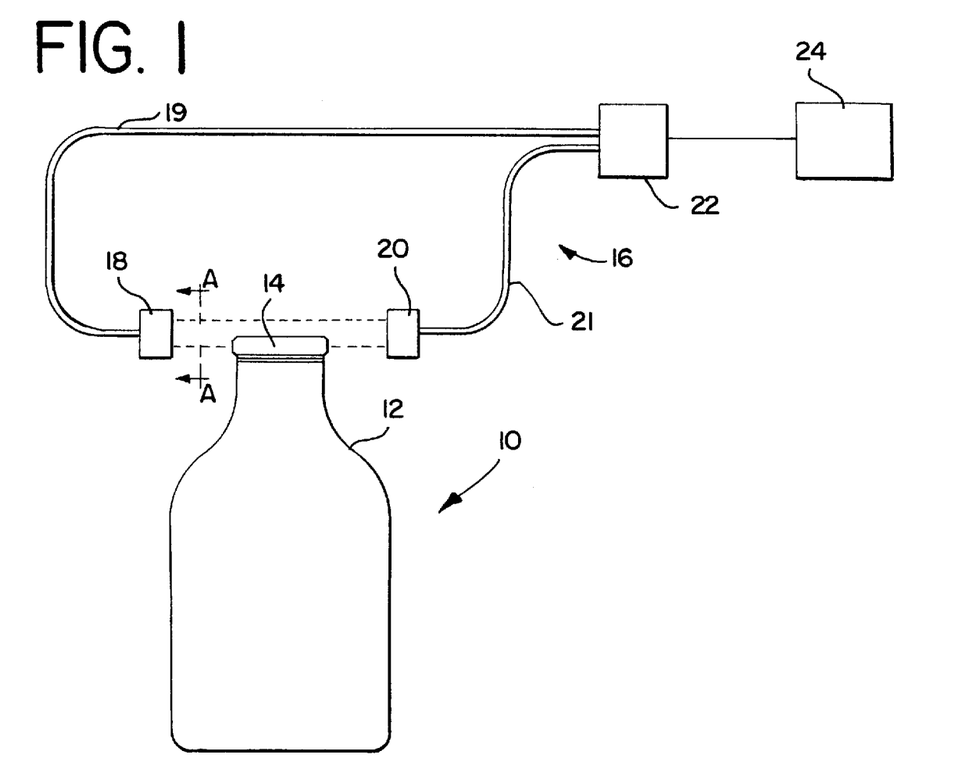
FIG. 1 is an illustration showing several components of a preferred linear optical sensor system of the present invention in relation to a container and closure under inspection.
Figure 2A:
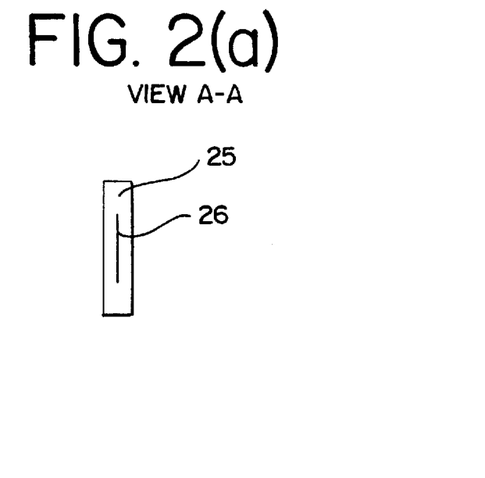
FIG. 2(a) is a illustration showing features of the optical heads shown in FIG. 1.

The linear optical sensing system of the preferred embodiment is illustrated in FIG. 1. A package 10 is represented by a container 12 having a closure 14 set thereon. For the purposes of this description it may be assumed that the product closure is being transported on a conveyor belt. Two fiber optic heads 18 and 20 are positioned relative to the package 10. As illustrated in FIG. 2a, the fiber optical heads include an optical head housing 25 having a vertical, rectangular slit 26, narrow in the horizontal direction and longer in the vertical direction. Optical fibers are arranged along the length of optical slit 26. The optical fibers associated with optical heads 18 and 20 are separately bundled and in communication with optical sensor 22. Optical sensor 22 is preferably in communication with a processor 24, such as a personal computer, or a microprocessor circuit.

Figure 2B:
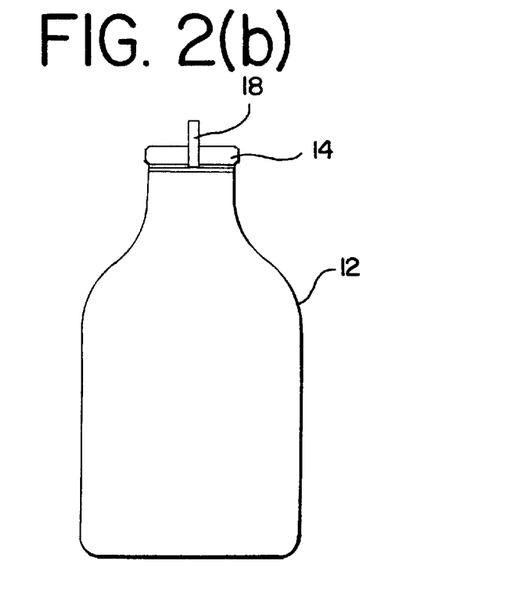
FIG. 2(b) is an illustration showing a preferred positional relationship between an optical head of FIG. 1 and a closure.

In the preferred embodiment, one optical head 20 functions as a light source and the other optical head 18 functions as a light receiver. As illustrated in FIGS. 1 and 2B, preferably the optical heads 18 and 20 are positioned so that the lower edge of the optics are at a vertical position near the vertical height of the closure's vertical midpoint. In the preferred embodiment, the sensor heads 18 and 20 are spatially aligned and facing each other at a distance of 150 mm, the slit 26 is 0.01 inches in width and 0.5 inches in height. The optical heads are 0.75 inch long and 1 inch deep. The portion of the optical fibers outside the optic heads are preferably grouped in bundles having a diameter of 0.079 inch and encased in PVC monocoil 19 and 21, having a diameter of 0.185 inch and a length of 48 inches.

In the inspection system, the sensing heads are located over the conveyor, looking across the path of travel of the package. Package 10 is transported by the conveyor between the optic heads 18 and 20 and light transmitted across the path is detected by the fiber optical head receiver 18. In an alternate embodiment, the optic heads 18 and 20 are transported horizontally past a stationary product closure 10. In still another embodiment, both the product enclosure and the fiber optic heads are in motion.

In the preferred embodiment, as a package with a closure travels along the conveyor, the closure interrupts portions of the light beam between the fiber optic heads. Light that is blocked by the closure 14 as it moves between the fiber optic heads 18 and 20 is not received by the fiber optic head receiver 18. Because the fibers are aligned vertically, the amount of light received by the fiber optic head is highly dependent upon the vertical position and attitude of the closure. The magnitude of the signal provided by optical sensor 22 along the length of the closure thus provides relative detail regarding the position and orientation of the closure. The optic sensor 22 provides an analog signal that varies in proportion (or inverse proportion) to the light received in the receiver sensing head. In the preferred embodiment, the optical sensor provides an analog output signal that is proportional to the amount of light received by the fiber optic head receiver 18. A properly applied closure generates a sensor signal that would be identified as "nominal". An improperly seated closure rides higher in the package and blocks more light between the optic sensor heads. A package with no closure blocks less light.

The voltage provided by the optical sensor 22 that corresponds to a container having a properly applied closure thereon may be set by initializing the system. The system may be initialized by providing a container having a properly applied closure between the fiber optic heads and adjusting the height of the fiber optic heads to adjust the voltage provided by the optical sensor.

In the present embodiment, an opposed mode (through-beam) optical sensor with fiber optics is utilized, however, other types of optical sensors may be used without departing from the scope of the present invention. The preferred optical sensor is the Smarteye® analog DC proportional model, having part number HSAQF1, the data sheet of which is published in a catalog entitled "Photoelectric sensors, fiber optic light guides and controls" published in 1996 by Tri-Tronics, of Tampa Florida, hereby incorporated herein by reference. This sensor has a high intensity infrared light source and a near linear output with a relatively fast response time (rated at 500 microseconds). The fast response time is preferred to handle the higher packaging inspection rates. The near linear output provides better resolution of the package closure profile and provides less of a need to adjust the settings for different container heights.

As discussed below, the position and attitude of the closure 14 on the container 12 is determinable from the signal provided by optical sensor 22. A conventional signal processor may be programmed to translate signal levels into a pass/fail condition, control an inspection system interface display, activate a discharge/reject system, record statistical data for analysis, and perform other container inspection system recording, communication, and control functions.

Figure 3A:
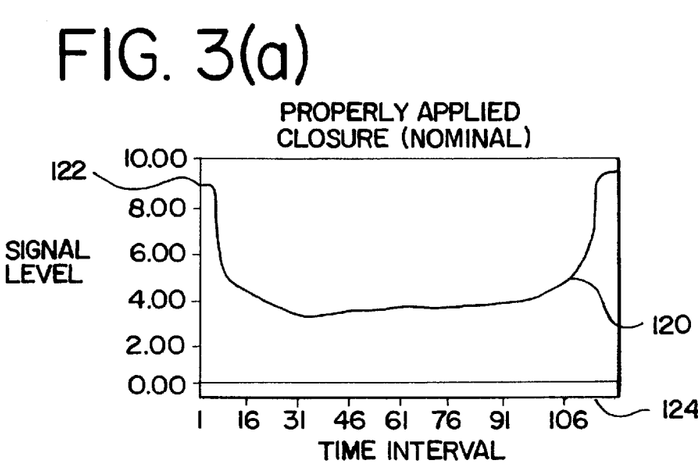
FIG. 3(a) shows the linear profile of a properly applied closure, generated by the system of the present invention.

Referring now to FIGS. 3(a)–3(d), signal traces of a single package having a closure set in different positions is shown. The signal trace of a properly set closure is shown in FIG. 3(a). The trace shows the analog voltage output of optical sensor 22 along the vertical axis 122. The analog voltage output is shown as a function of time along the horizontal axis 124. As shown in FIG. 3(a), a properly set closure provides a relatively uniform trace for the time interval corresponding to the leading edge of the container intersecting the plane between the fiber optic heads 18 and 20 to the trailing edge intersecting the plane. The voltage signal level corresponding to a properly seated closure (4.0 volts in this example) may be predetermined by placing between the fiber optic heads a container with a properly seated closure. The vertical displacement of the fiber optic heads may thereafter be adjusted until the voltage level provided by the optical sensor 24 is (preferably) within 40–60% of the full scale voltage. The signal conditioning and leveling circuit, discussed below, may be used to further adjust the voltage level that corresponds to a properly seated closure.

Figure 3B:
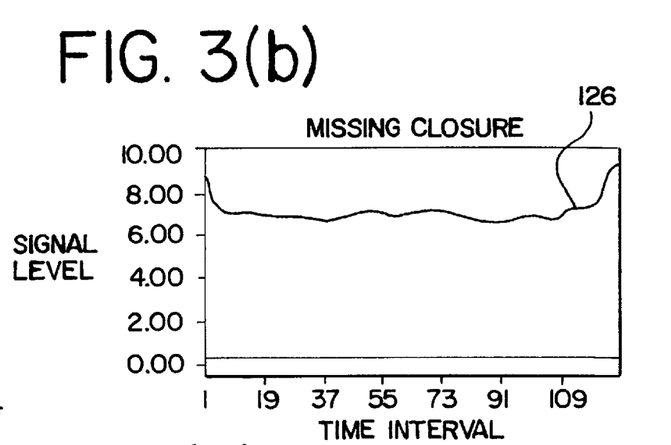
FIG. 3(b) shows the linear profile of a container missing a closure, generated by the system of the present invention.

FIG. 3(b) shows a linear optical sensor trace 126 for a container having a missing closure. As shown, the output voltage for a container in this example is approximately 7.0 volts, or 3.0 volts higher than the output voltage for the properly seated closure discussed above. The higher voltage level corresponds to more light being received by the optic sensor head, as there is no closure to block light provided by the light source.

Figure 3C:
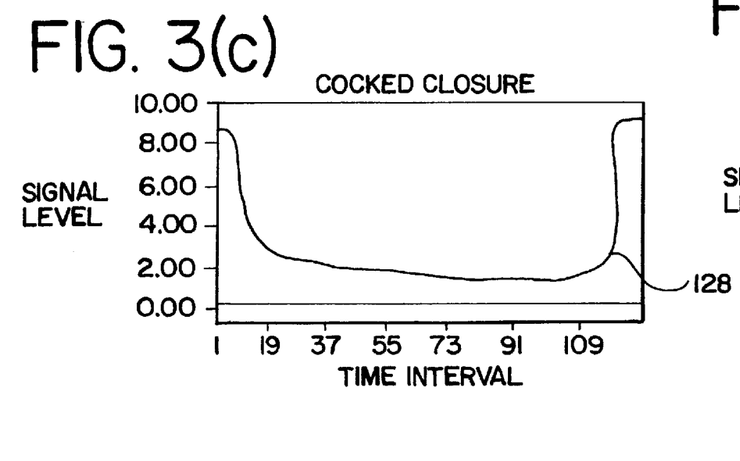
FIG. 3(c) shows the linear profile of a cocked closure, generated by the system of the present invention.

FIG. 3(c) shows a linear optical sensor trace 126 for a container having a cocked closure. As shown, a cocked closure is indicated by a voltage level that changes as the optical head 18 scans the container. In this example, the voltage level decreases from about 3 volts to about 1 volt, clearly indicating that the closure is not horizontal.

Figure 3D:
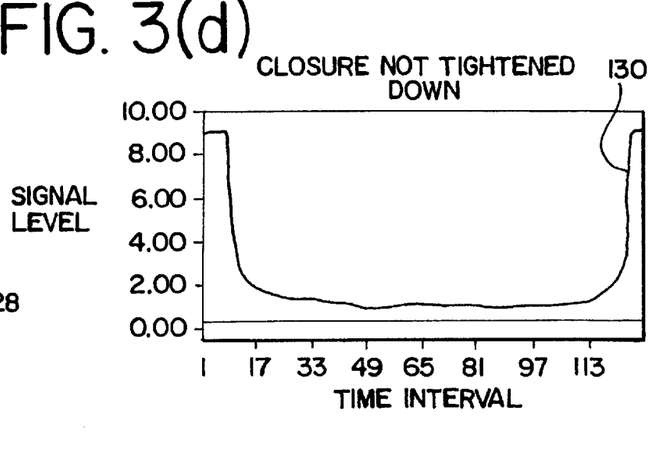
FIG. 3(d) shows the linear profile of a closure not tightened down on a container, generated by the system of the present invention.

FIG. 3(d) shows a linear optical sensor trace 126 for a container having a closure that is not tightened down. In this position, the closure prevents more light from the light source from reaching the optic head receiver. Thus, the voltage provided by the optic sensor is relatively lower (1.0 volt) than the voltage level provided from scanning a closure that is set properly.

In the presently preferred embodiment, the linear optical sensor provides an analog output signal to a processor 24. The processor is programmed to perform all inspections on the container based on the data received from the linear optical sensor. The processor samples the optical sensor signal and processes the digital samples for determining whether the closure is properly seated on the container, for rejecting the container if it is not, and preferably adding the data for at least each rejected container to an inspection database. An inspection database may be used for a variety of inspection, operation, and quality control purposes. For example, a maximum reject frequency may be predetermined and if the reject frequency exceeds that number, the processor may activate an alarm, stop the line, or otherwise communicate the condition to an operator via a user interface. The processor is also preferably programmable so that inspection improvements and system expansions may be accomplished through changes to processor software alone.

In the preferred embodiment, the processor is connected to an interface that includes a graphic touch-screen display which is programmed so that inspection system adjustments, such as optical head height, may be made via interactive computer assistance. The interface also preferably receives signals provided by the processor for providing a good/bad closure count, reasons for the most recent rejections, fault messages, a good closure pulse signal, one or more bad closure pulse signals, a bad closure alarm, a system fault signal, and other information. The interface may also be used to provide control signals from the processor to an external PLC or other control station. An external PLC or control station may be implemented in the system to provide additional inspection criteria. Preferably, the interface also includes a linear sensor signal graphic display for displaying sensor output.

Figure 9:
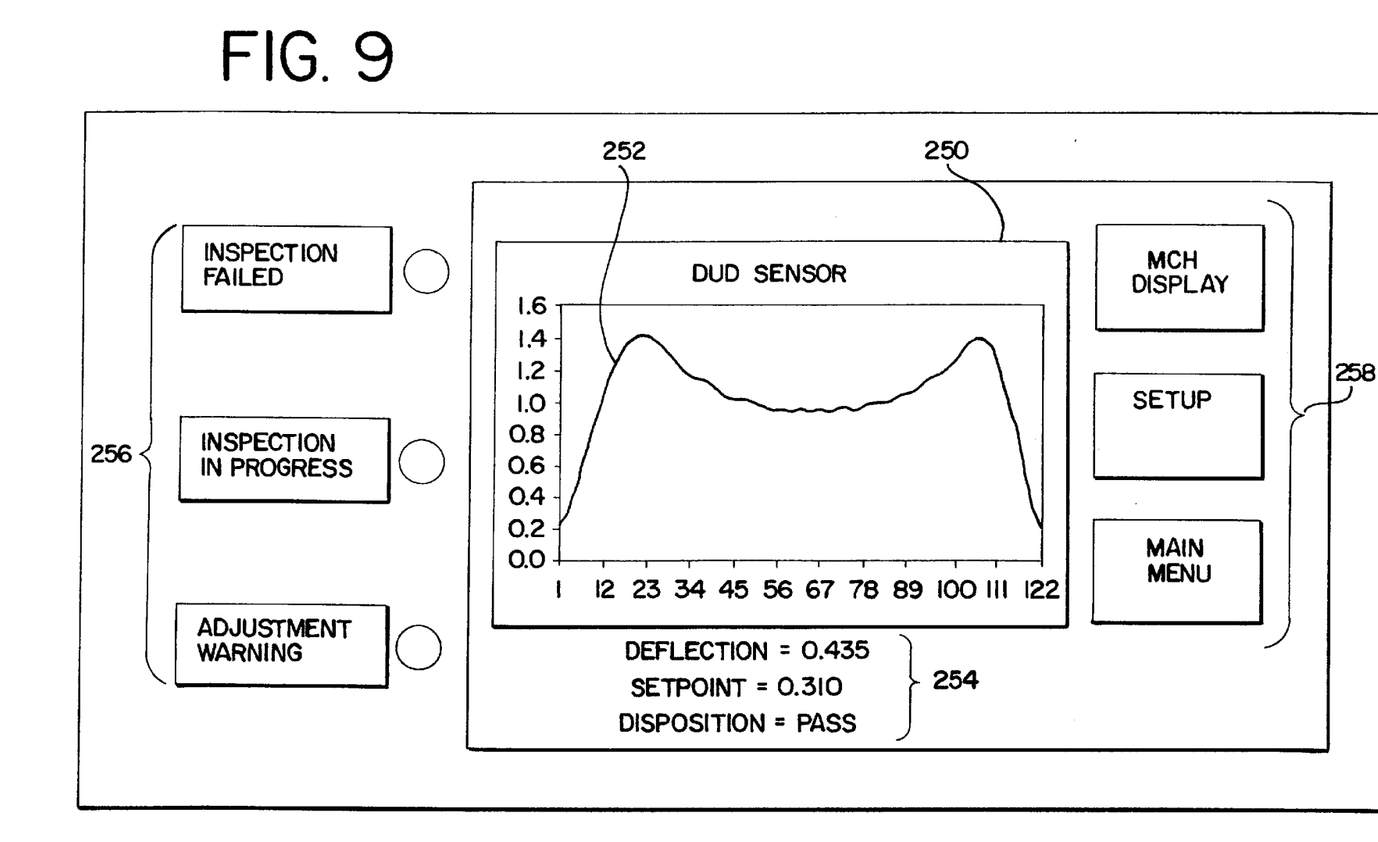
FIG. 9 is a illustration of a display for a linear optical sensor system interface.

An example of an interface display is shown in FIG. 9. The interface display includes a display section 250 for providing a trace display 252 and an alphanumeric display of trace characteristics. The interface display further includes a system status section for providing a visual indication of the status of the system. The interface also includes a plurality of control buttons 258, such as MCH (missing, cocked, high), setup, and main menu for controlling the display section.

Figure 7:
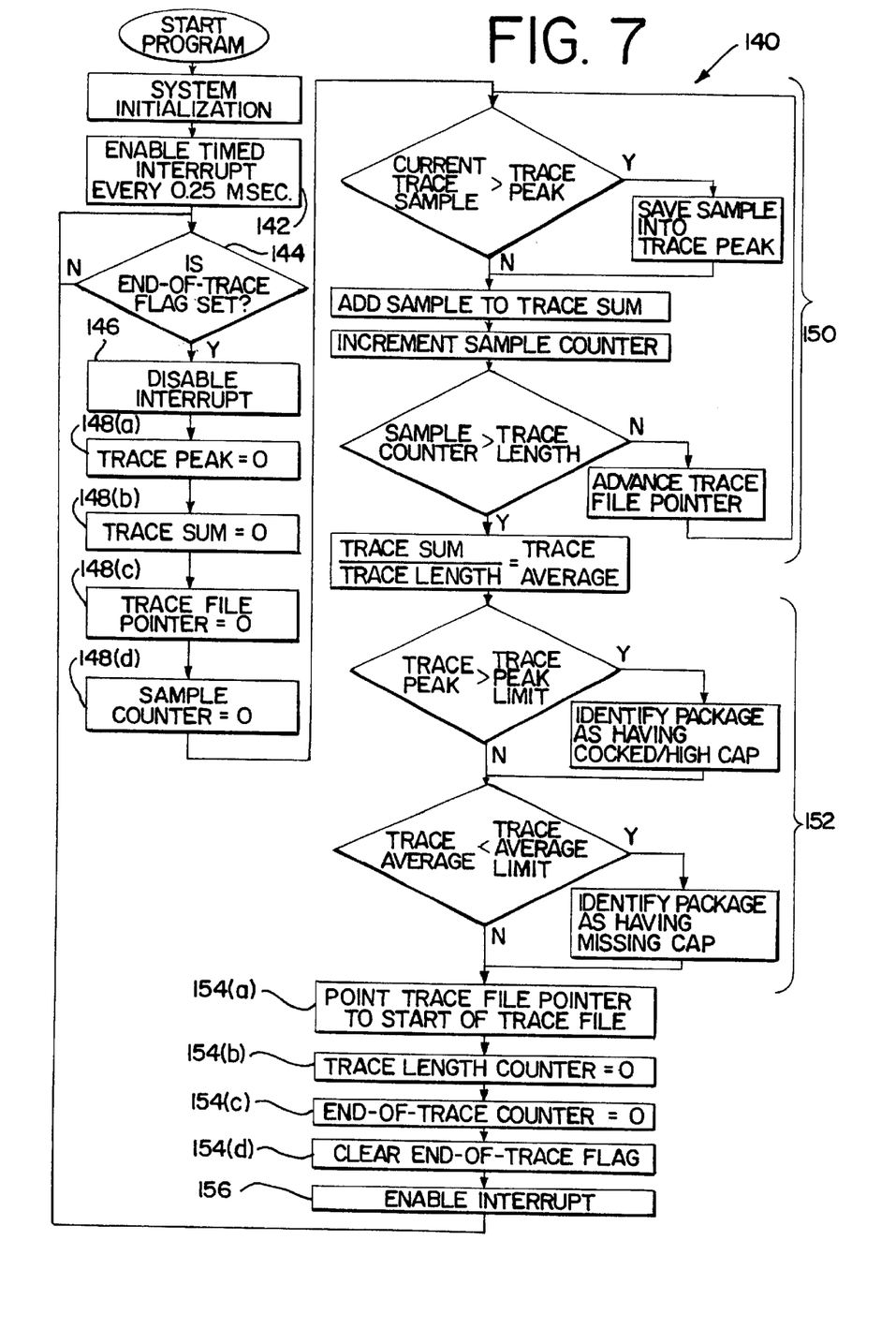
FIG. 7 is a flow diagram of a processor routine for a preferred linear optical sensor system of the present invention.

In the preferred embodiment, the processor 24 is programmed in accord with the flow chart shown in FIG. 7. The processor periodically samples the analog signal provided by the optical sensor 22, and determines, based on the sample value and sample number, whether a container is within the optical scanning field and whether the package has a cocked/high cap or a missing cap A trace peak limit parameter is set and pre-stored as a threshold for identifying closures set too high on the container (cocked cap or cap too high), and a trace average limit is set and pre-stored for identifying containers with missing caps, as explained below. In an alternate embodiment, only the peak value of a trace is compared with a minimum limit. If the peak value of the trace is less than the minimum limit, the processor identifies the container as having a missing closure.

Preferably, the processor samples the optical sensor output every 0.25 millisecond. At a conveyor line speed of 250 feet/minute, a 0.25 millisecond sampling frequency will produce about 100 samples for even a small closure, such as a ketchup cap. Using the trace data, the processor determines the length (number of samples) and end of a trace for each closure. An end-of-trace flag is set when the container has left the scan field. A trace-length counter is utilized for defining the length of the closure (total number of samples for a given closure) and for determining the position and attitude of the closure. Trace length for a closure is dependent upon the sampling frequency, the width of the closure, and the speed at which a closure/container moves relative to the linear optic receiver.

Figure 8:
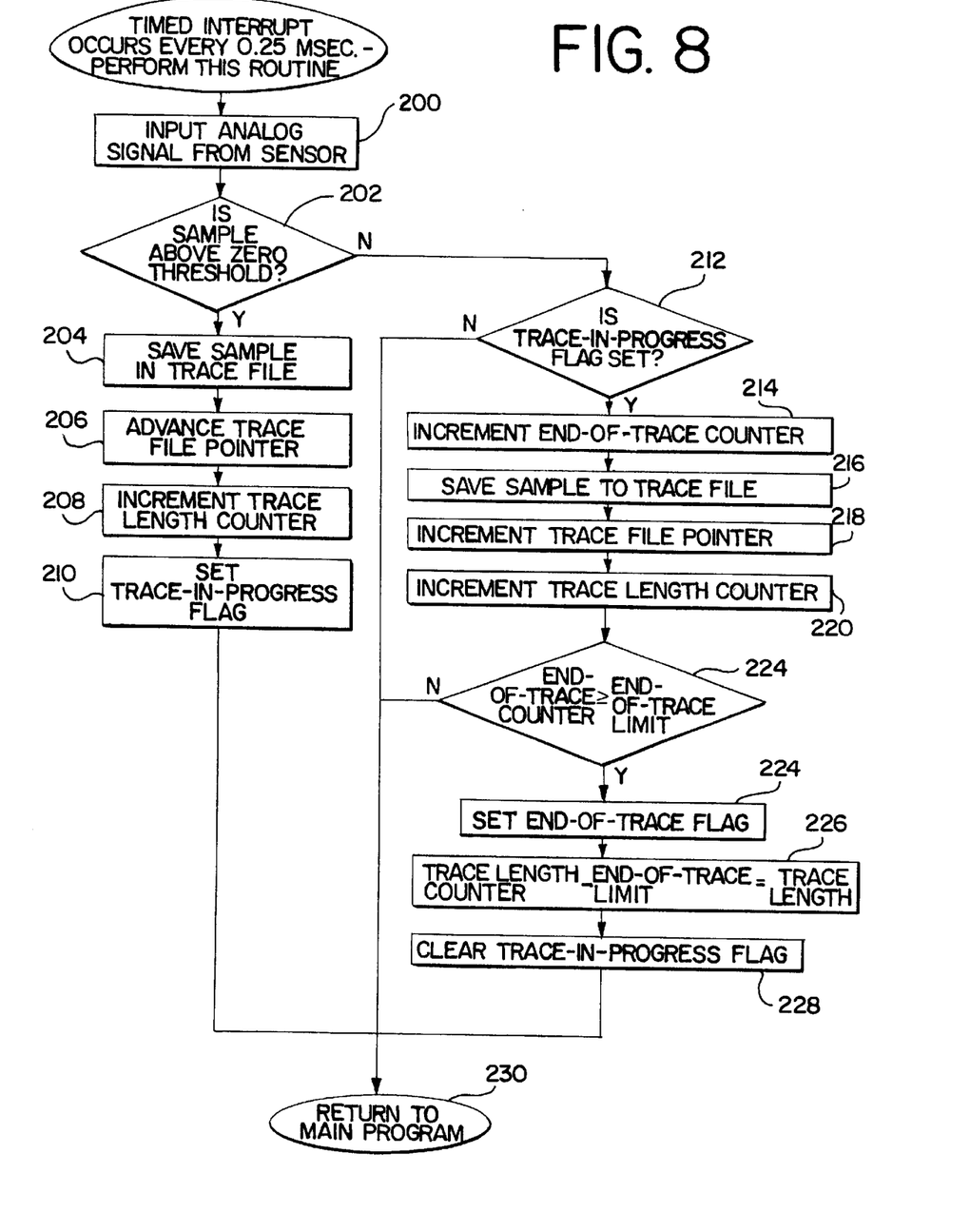
FIG. 8 is a flow diagram of a processor interrupt routine for a preferred linear optical sensor system of the present invention.

Referring to FIG. 8, a sample is first compared 202 with a threshold level (in this example, 0 volts) for determining if a container is within the scan field. In the present embodiment, an uninterrupted beam of light provides a low analog signal (and thus low sample) and an interrupted beam of light provides a high analog signal. The threshold level is set so that if a container is not in the scan field, the analog signal produced by the optic sensor will not be greater than the threshold level. In an alternate embodiment, an uninterrupted beam of light provides a high analog signal (and thus a high sample) and an interrupted beam of light provides a low analog signal. It should be noted that, for clarification purposes, FIGS. 3(a)–3(d) are shown in accord with this alternate embodiment.

Returning to FIG. 8, if the present sample is not above the threshold (indicating no container within the scan field), a trace-in-progress flag is reviewed 212 to determine whether the system has previously established that a container is not within the scan field. If the system has previously determined that a container is not within the scan field, the interrupt routine is exited 230. If the trace-in-progress flag is set, an end-of-trace counter is incremented 214.

The end-of-trace counter allows the system of the present embodiment to distinguish between a sample that is below the threshold level due to the absence of a container within the scan field, from a sample that is below the threshold level due to noise in the analog signal from the optic sensor. In the present embodiment, twelve consecutive samples below the threshold must be received before the system sets an end-of-trace flag 224 indicating that there is no container within the scan field. The end of trace parameter (twelve in this example) is predetermined by an operator and stored as an end-of-trace limit. The processor compares the end-of-trace counter with the end-of-trace limit at 222. In addition to incrementing the end-of-trace counter, the system saves the present sample to the trace file 216, increments a trace file pointer 218, and increments a trace length counter 220.

When the end-of-trace counter is equal to (or greater than) the end-of-trace limit, the end-of-trace flag is set 224. The trace length is then calculated as the difference between the trace length counter and the end-of-trace limit 226, and the trace-in-progress flag is cleared 228 to indicate that the trace is complete.

If the sample from the analog sensor signal indicates that a container is within the scan field, the sample is saved in the trace file 204, the trace file pointer is incremented, the trace length counter is incremented 208, and the trace-in-progress flag is set. Processor control is then returned to the main program 230.

While the interrupt routine is preferably set to occur every .25 millisecond, in the main program (FIG. 7) the processor continuously reviews for an end-of-trace flag 144. After the interrupt routine sets the end-of-trace flag, the processor initiates a routine for analyzing the stored trace data: the interrupt is disabled 146, trace peak and trace sum parameters are reset to zero 148(a) and 148(b), and a trace file pointer and sample counter are set to zero 148(c) and 148(d). Next, each sample is reviewed to find the trace peak value 150. Also, each sample value is added to a trace sum. When the sample counter is greater than the trace length, the trace average is calculated, the trace peak is compared to the trace peak limit for identifying cocked or high caps, and the trace average is compared to the trace average limit to determine if the closure is missing 152. Finally, the trace file pointer is reset to the start of the trace file 154(a), the trace length counter and the end-of-trace counter are reset to zero 154(b) and 154(c), the end-of-trace flag is cleared 154(d), and the interrupt routine is enabled 156.

Thus, the processor stores a number of samples for defining the trace of a closure as the closure passes the linear optical head. The peak sample value is referenced to determine if the closure is set high or cocked on the container. A sample average value is referenced to determine if the closure is missing. As discussed below, the processor may be further programmed to eject missing, high, or cocked closures.

Figure 5:
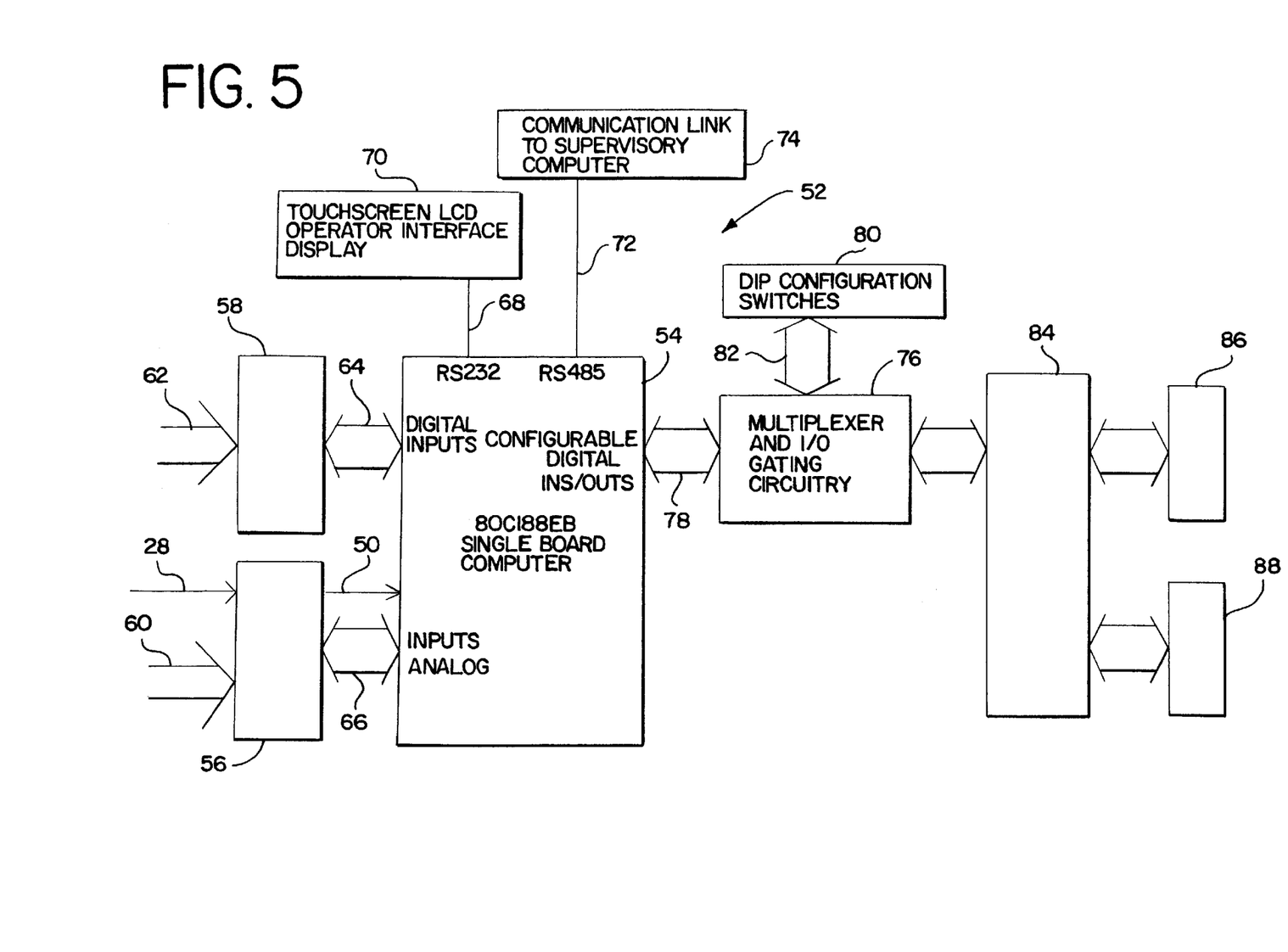
FIG. 5 is a block diagram showing several components of a package inspection system that includes the linear optical sensor system of the present invention.

Referring to FIG. 5, therein is shown a block diagram of a container inspection system 52 that includes the linear optical inspection system of the present invention. The container inspection system includes a processor 54 preferably programmed in accord with the flow charts of FIGS. 7 and 8 for controlling the linear optical inspection system.

The processor may be further programmed for controlling other components in the container inspection system. For example, in addition to receiving output from the optic sensor 22 via conditioning circuit 56, the processor 54 may receive other analog and digital sensor signals. Processor 54 is also preferably programmable for providing output signals for controlling the operation of the package inspection system, recording data, and communicating with an operator interface. Processor 54 may be further programmed for communicating with other computers and/or control networks, such as programmable logic controllers.

Inputs to processor 54 preferably include a plurality of signals provided by analog and digital sensors in a package inspection system. Analog sensors may include a non-contact proximity sensor for measuring the panel deflection of a closure such as a metal cap, a CCD laser sensor for measuring the panel deflection of closures such as plastic caps, sensors for detecting the fill level of a container, and other sensors.

Processor 54 preferably receives input signals from digital sensors such as an ultrasonic proximity sensor which may detect broken glass, crushed or downed plastic containers and the like that would otherwise go undetected by other sensors. Other digital sensors include an ultraviolet tamper band detection sensor that detects the presence/absence of ultraviolet luminescent tamper bands, a foil seal detection sensor for detecting the presence/absence of a foil seal underneath a plastic container closure, label detection sensors for detecting the presence/absence of a plurality of spot and/or partial wrap labels, and other sensors.

Outputs from analog sensors 60 are preferably conditioned by analog signal conditioning circuitry 56, which may also include circuitry for conditioning the signal provided by the optic sensor 22. Outputs from digital sensors 62 are preferably conditioned by digital signal conditioning circuitry 58.

The processor 54 may be programmed for performing all of the requisite inspection, detection, recording, rejection, communication, and other functions desired in a container inspection system. Conditioned analog and digital input signals 66 and 64 may be processed in accordance with conventional methods for inspecting container/closure assemblies. However, the conditioned linear optical sensor input signal 50 is preferably processed in accordance with the present embodiment of the invention, as discussed above.

Microprocessor 54 also preferably includes communication ports for receiving and providing operator interface communication signals from and to an operator interface 70 and for communicating to one or more data processor systems, such as a supervisory computer 74.

Preferably, operator interface 70 includes a touch screen LCD display for providing interactive computer assisted adjustments, sensor signal graphic displays, satisfactory/unsatisfactory closure counts, a display of reasons for rejected containers and/or closures, and other messages related to the system. Microprocessor 54 may be further configured for communicating with additional circuitry 86 and 88. A DIP configuration switch network 80 is preferably implemented with a multiplexor and gating circuitry 76 for driving a code set on the DIP configuration switch to the microprocessor input. The DIP switches are manually set in accord with the options and sensors that are installed in the inspection system. The microprocessor determines a mode of operation based on the DIP configuration. The multiplexor and input/output gating circuitry 76 may also be connected to an optical isolator 84 for controlling assembly line inspection devices such as solenoids and PLC equipment. In the preferred embodiment, the microprocessor 54 is an 80C8188EB single board computer distributed by Microsystems in California.

Figure 4:
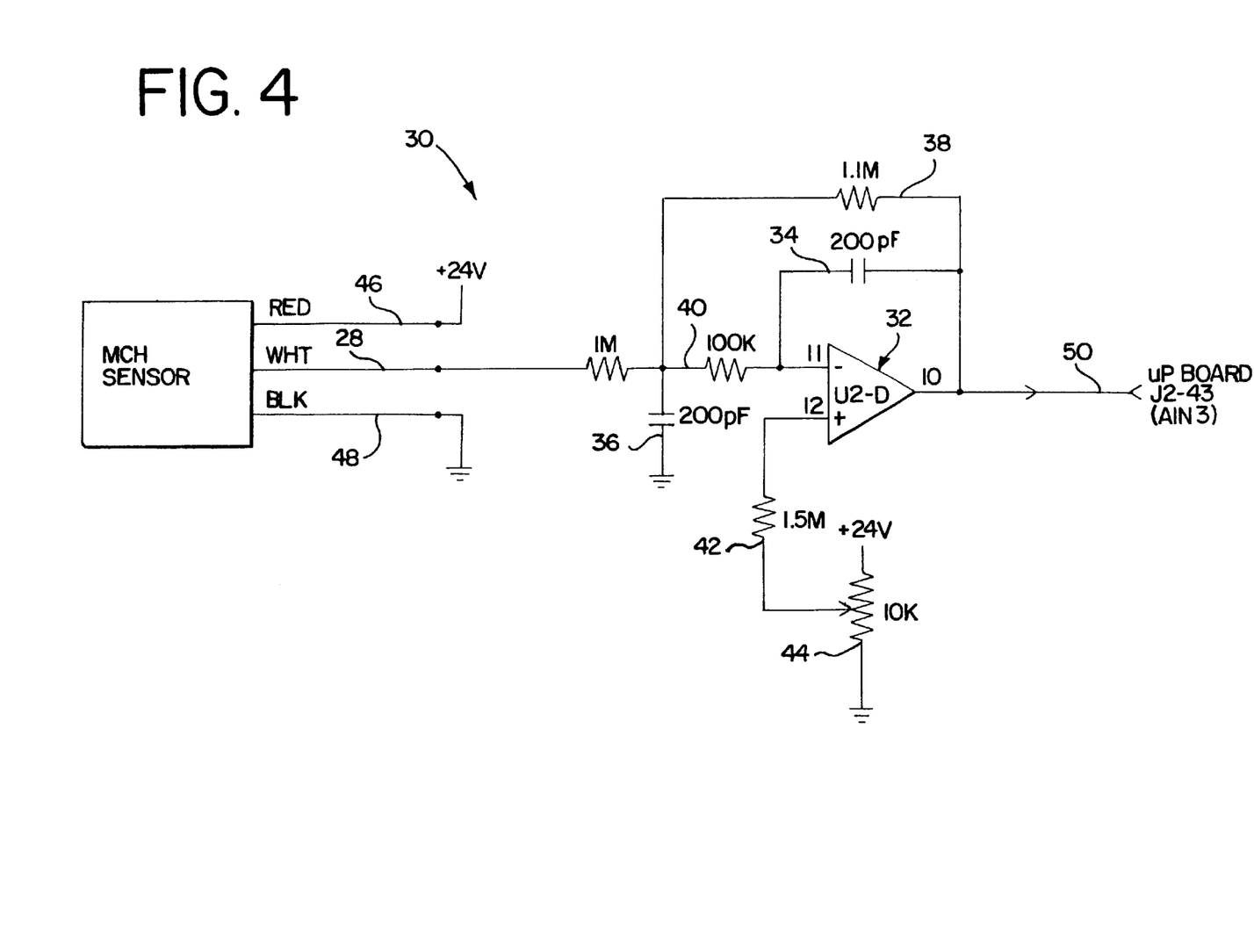
FIG. 4 is a schematic diagram of a filter and buffer circuit for providing an optical sensor analog output signal to a processor input terminal.

Referring to FIG. 4, therein is illustrated a signal conditioning circuit 30 for receiving the output of optical sensor 22 and filtering and scaling the analog signal for input to the microprocessor. Signal conditioning circuit 30 includes an op amp 32 for receiving the analog output from optical sensor 22 and driving an output signal to a microprocessor. A feedback capacitor 34 and a ground capacitor 36 are provided for filtering noise. Resistors 38, 40, 42 and 44 control the gain and offset of the signal conditioning circuit 30. The output of the signal conditioning circuit 30 is provided to the microprocessor via conductor 50. Also shown in FIG. 4 are the power supply terminal 46 and ground terminal 48 for the optical sensor 22.

Figure 6:
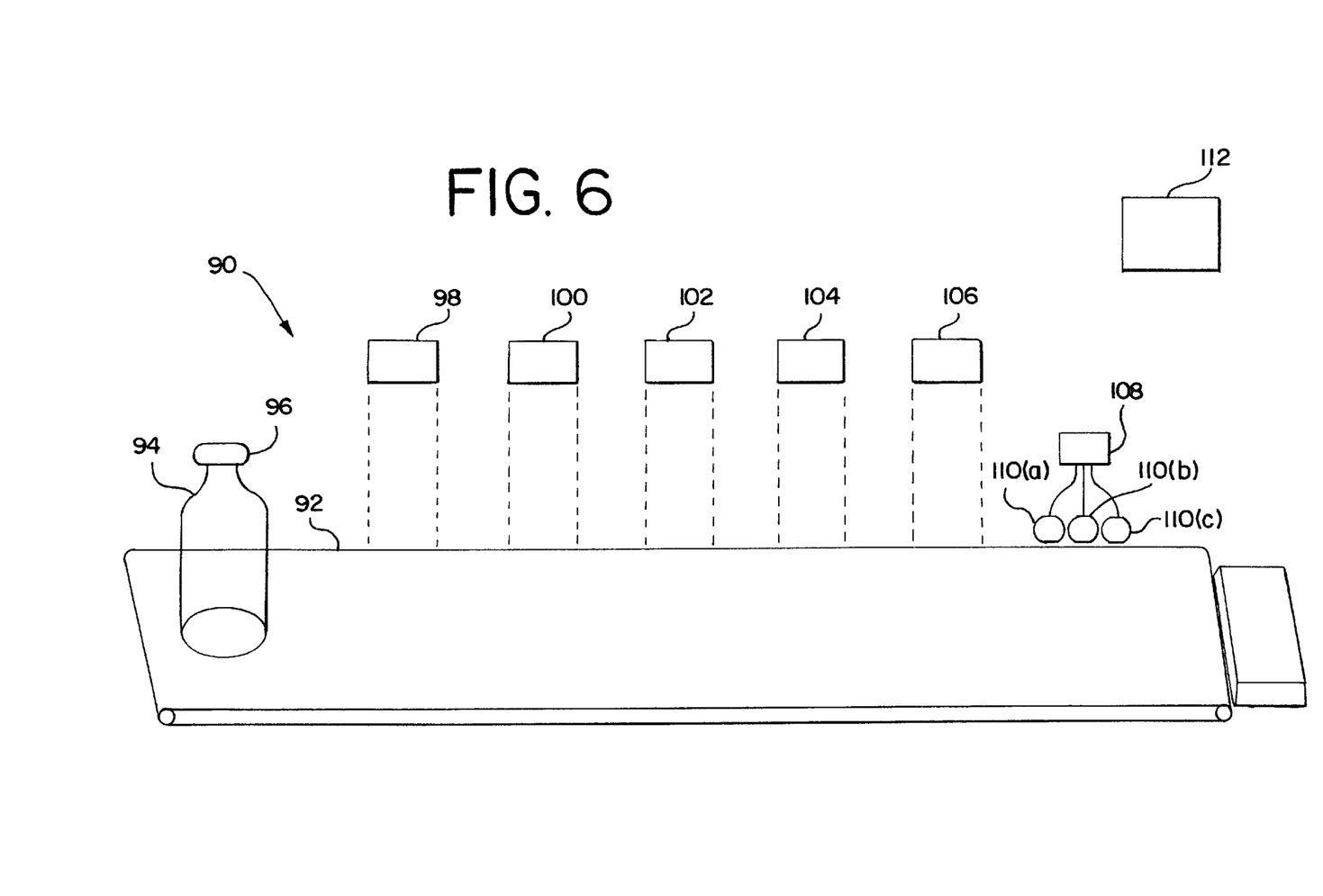
FIG. 6 is an illustration showing several components of a package inspection system that id includes the linear optical sensor system of the present invention.

Next, a general description will be provided of a preferred package inspection system including the linear optical sensor of the present invention. Referring to FIG. 6, therein is shown a package inspection system line 90. The inspection system 90 includes a conveyor belt 92 for transporting a container 94 having a closure 96 set thereon. Inspection system 90 includes a plurality of sensor stations 98, 100, 102, 104, and 106. One or more characteristics or conditions of the container and/or closure are tested for or detected by an appropriate sensor at each station. In this example, a dud detector 98, optic sensor 100, label sensor assembly 102, foil detector and ultraviolet band sensor assembly 104, and fill level and cap color detector 106 are included along the container/closure assembly travel path.

The dud detector provides a measurement at the top of a closure for determining whether the container is properly vacuum sealed. The dud detector measures the panel deflection of the closure, which, if properly sealed, is deflected inward a predetermined distance. The panel deflection is determined by measuring the distance from the sensor to the top of the closure. The dud detector 98 is preferably a laser type detector positioned 35 mm above a horizontal plane passing through the center of a properly seated closure. Preferably, the laser dud detector is fixed with respect to the optical sensor heads 18 and 20 and may be simultaneously adjusted therewith. The dud detect sensor is preferably a CCD laser displacement sensor having model no. LK-031, available from Keyence of Woodcliff Lake, N.J.

In an alternate embodiment, an inductive proximity detector is utilized as the dud detector 98. The position of the inductive proximity detector may be adjusted with respect to the optical sensor heads for measuring panel deflection. The vertical position of the optical sensor heads may also be fixed with respect to the inductive proximity detector and adjusted therewith. The preferred inductive dud detector is available from Balluff of Florence, Ky., and has model no. BAW-018-PF-1-K-5. For small button closures, the preferred proximity detector is model no. NJ4-12GK-N available from Pepperl+Fuchs of Twinsburg, Ohio. Preferably, the output of the dud detector is provided to buffer and filter circuits to eliminate signal noise and adjust the analog voltage to within a range of 0–10 volts for input to the processor.

Referring again to FIG. 6, a second scan station includes the optic sensor of the present invention, as well as a sensor for providing a signal indicative of a broken or crushed container. The downed container sensor is preferably an ultrasonic sensor positioned below the optic heads and adjustable in the vertical and horizontal (closer to and further from the container) directions. The ultrasonic sensor preferably has a range of 1–7 inches for detecting the presence of an intact container. The ultrasonic sensor provides a digital output indicative whether an object is detected in the scan field. If a container is detected where not expected, the processor interprets this condition as indicative of a broken or crushed container. The preferred ultrasonic sensor is Model SM600, part no. SM600A-796-00FP available from Hyde Park of Dayton, Ohio.

The analog output of the optic sensor is preferably provided to the buffer circuit shown in FIG. 4, as discussed above. The digital output of the downed container sensor is preferably provided to the processor through an opto-isolator.

Preferably, the optic sensor heads are interlinked and manually adjustable so that a single adjustment can be made to adjust the vertical position of both heads simultaneously, and automatically adjustable via a user interface (preferably touch-screen) and processor control for finer adjustments.

A third scan station includes a plurality of sensors for detecting the presence/absence of container labels. In the present embodiment, up to four sensors are directed at spacial locations for viewing predetermined locations on a container. If more than one sensor is used, the sensors preferably view along the same vertical centerline and are adjustable in the vertical and horizontal directions. Sensors can be arranged to inspect multiple spot labels and many partial wrap labels. Each label sensor provides a digital output indicative of the presence/absence of a label to the processor through an optoisolator. The preferred label sensor is a MiniSight Photoswitch, manufactured by Allen-Bradley.

A fourth scan station includes sensors for detecting the presence of safety seals and bands, such as a foil over a container opening and/or a tamper band around the closure and container neck, for example. In the present embodiment, the tamper band is doped with a substance that luminesces when exposed to ultraviolet light.

The foil detector preferably comprises a vertically adjustable proximity sensor having a digital output. The vertical position of the foil detector is important as it is desirable to position the sensor as low as possible to accurately detect foil on a passing container. The proximity sensor is preferably mounted to allow for vertical deflection if the sensor is contacted by a passing container. The preferred foil sensor is Uprox model CP80, having part number Ni75U-CP80-APX62, available from Turck, Inc., of Minneapolis, Minn.

The ultraviolet band detection sensor is typically positioned a distance of one to two inches from the tamper band on a passing container and is adjustable in the horizontal and vertical directions. In the preferred embodiment, the center of the ultraviolet sensor lens is positioned directly under the center of the foil detector and provides a digital output indicative of the presence/absence of a safety band. A preferred ultraviolet sensor is model LUT3-650, available from Sick in Eden Prairie, Minn. Preferably, the UV band sensor and the foil proximity sensor are electrically isolated from the processor through respective optoisolators.

One or more additional scan stations may optionally be included in the inspection system. Additional scan stations may include sensors for detecting other attributes of the container/closure assembly. For example, an additional sensor may detect the fill level (underfill or overfill) of the container. Also, sensors may be used for determining the color of the closure, thus identifying containers having closures of a different design or wrong color.

FIG. 6 also shows a container reject station that includes an ejector controller 108 and one or more ejectors. In the preferred embodiment, the system is assignable for having containers with particular defects rejected by particular ejectors.

The illustrated embodiment includes three ejectors 10(a), 110(b), and 110(c). The reject controller station is preferably controlled by the system computer or processor 112, which receives input signals from the sensors within each scan station, and ejects defective containers into respective receptacles based on the defective condition. An encoder may be linked to the conveyor for providing data to the microprocessor for coordinating conveyor speed and container position with ejector activation. In a preferred embodiment, an optical disk encoder monitors the rotary motion of a conveyor shaft and is connected to the system processor through an optoisolator. An encoder is especially useful in applications where the conveyor changes speed regularly, or where eject control must remain accurate during starts and stops. If an encoder is not used, eject control is time-driven.

The present invention has been described in the context of a preferred and alternate embodiments, as well as a system into which the invention may be incorporated. It is apparent to those skilled in this art, however, that modifications and variations to the disclosed embodiments can be made without departing from the spirit and scope of the invention. Accordingly, this invention is to be construed and limited only by the scope of the appended claims.

I claim:

1. A linear optical sensor system for generating a trace profile of a closure section of a package, said linear optical sensor system comprising:
   a plurality of optical fibers arranged in a substantially linear, vertically oriented configuration, said fibers defining a scan area for receiving light transmitted at said closure section;
   a transport mechanism for transporting the package through the scan area; and
   an optical sensor for receiving said light from said optical fibers as the package is transported through the scan area and for responsively generating an output signal, the magnitude of which is indicative of the instantaneous quantity of light received;
   an analog-to-digital converter for sampling said output signal and for generating a plurality of digital samples, said plurality of digital samples comprising a trace profile of the closure section of the package.

2. The linear optical sensor system of claim 1 further comprising:
   a processor for receiving and storing said plurality of digital samples and programmed to determine, based upon the stored digital samples, if the closure is properly set on the package.

3. The linear optical sensor system of claim 1 further comprising:
   a first optical head comprising said plurality of optical fibers; and
   a second optical head for transmitting a vertically oriented, substantially linear beam of light to said first optical head.

4. The linear optical sensor system of claim 2 wherein said processor identifies packages having cocked and high closures by comparing a peak trace profile digital sample value to a predetermined trace peak limit value and identifies packages having missing closures by calculating a trace average digital sample value and comparing said average digital sample value to a trace average limit, and wherein said cocked and high closures have a peak trace profile digital sample value greater than said predetermined trace peak limit value and said packages having missing closures have a trace average digital sample value less than said trace average limit.

5. The linear optical sensor system of claim 2, further comprising:
   an operator interface for receiving display signals from said processor and for providing a display of said trace profile.

6. The linear optical sensor system of claim 2, further comprising at least one ejector controlled by said processor.

7. The linear optical sensor system of claim 1 further comprising
   a processor for receiving said plurality of digital samples, determining the digital sample having the largest magnitude within said plurality of digital samples, and determining, based upon a comparison of the digital sample having the largest magnitude with a minimum limit magnitude, if the closure is missing.

8. A system for generating a plurality of digital data samples indicative of the vertical position of a closure on a container passing through an inspection station, said system comprising:
   a light source configured for horizontally projecting a beam of light, said beam of light being substantially linear and vertically oriented;
   a substantially linear and vertically oriented light receiver for receiving said substantially linear beam of light as said closure passes through said inspection station;
   an optical sensor connected to said light receiver for generating an analog signal, the magnitude of said analog signal proportional to the amount of light received; and
   a processor for receiving and sampling said analog signal, thereby generating a plurality of digital data samples comprising a trace profile for said closure.

9. The system of claim 8 wherein said processor samples said plurality of digital data samples at a rate of one sample every approximate 0.25 millisecond and stores said samples in a data memory, said processor storing at least 100 samples for the closure.

10. The system of claim 8 further comprising a predetermined zero threshold value and wherein said processor identifies a trailing edge of said closure with a one of said plurality of digital data samples generated immediately prior to the generation of twelve consecutive digital data samples having a value below said predetermined zero threshold.

11. The system of claim 8 wherein said light source and said light receiver comprise a first fiber optic head and a second fiber optic head, respectively.

12. The system of claim 11 wherein said first fiber optic head is further defined as approximately 0.75 inch long and having an aperture therein 0.01 inch in width and 0.5 inch in height.

13. The system of claim 8 further comprising a signal conditioning circuit for receiving said analog signal generated by said optical sensor, for filtering and scaling said analog signal, and for providing said filtered and scaled analog signal to said processor for sampling.

14. A method for determining whether a closure is properly seated on a container conveyed through a package inspection station in a first horizontal direction, said method comprising:
   projecting a vertically oriented and rectangular beam of light to said package inspection station in a second horizontal direction, said second horizontal direction substantially perpendicular to said first horizontal direction receiving said vertically oriented and rectangular beam of light;

generating a trace profile of said closure area as said package moves through said scan area, wherein said trace profile corresponds to the vertical orientation of said closure; and determining, based upon said trace profile, whether said closure is properly seated.

15. The method of claim 14 further comprising determining, based upon said trace profile, whether said package has a missing closure.

16. The method of claim 15 further comprising calculating a trace average for said container based upon said trace profile and comparing said trace average to a predetermined trace average limit for determining whether said package has a closure thereon.

17. The method of claim 14 wherein said generating step comprises:

generating an analog signal responsive to the quantity of light received by a light sensor, said quantity of light received by the light sensor dependent upon the position of said closure; and sampling said analog signal to generate said trace profile.

18. The method of claim 14 wherein said determining step further includes determining a peak value of said trace profile and comparing said peak value to a minimum limit magnitude to determine if said closure is missing.

* * * * *